United States Patent
Marter (10) Patent No.: US 9,655,750 B2
(45) Date of Patent: May 23, 2017

(54) ATTACHMENT MECHANISM

(75) Inventor: Alex Marter, Southampton (GB)

(73) Assignee: DEPUY (IRELAND), Cork (IE)

( * ) Notice: Subject to any disclaimer, the term of this patent is extended or adjusted under 35 U.S.C. 154(b) by 454 days.

(21) Appl. No.: 14/239,502

(22) PCT Filed: Jun. 6, 2012

(86) PCT No.: PCT/GB2012/051271
§ 371 (c)(1),
(2), (4) Date: Feb. 25, 2014

(87) PCT Pub. No.: WO2013/024245
PCT Pub. Date: Feb. 21, 2013

(65) Prior Publication Data
US 2014/0172112 A1    Jun. 19, 2014

(30) Foreign Application Priority Data
Aug. 16, 2011 (GB) .................................. 1114059.7

(51) Int. Cl.
*A61F 2/38* (2006.01)
*A61F 2/46* (2006.01)
*A61F 2/30* (2006.01)

(52) U.S. Cl.
CPC .............. *A61F 2/4684* (2013.01); *A61F 2/389* (2013.01); *A61F 2002/30354* (2013.01); *Y10T 29/49872* (2015.01); *Y10T 403/54* (2015.01)

(58) Field of Classification Search
CPC ............ A61F 2/91; A61F 2/389; A61F 2/40; A61F 2/3868; A61F 2/28; A61F 2/4684
See application file for complete search history.

(56) References Cited

U.S. PATENT DOCUMENTS

| | | |
|---|---|---|
| 2,671,255 A | 3/1954 | Kember |
| 4,944,757 A | 7/1990 | Martinez et al. |
| 5,019,103 A | 5/1991 | Van Zile et al. |
| 5,047,058 A | 9/1991 | Roberts et al. |
| 5,152,797 A | 10/1992 | Luckman et al. |

(Continued)

FOREIGN PATENT DOCUMENTS

| | | |
|---|---|---|
| EP | 1415625 A3 | 5/2004 |
| EP | 1415625 B1 | 5/2006 |

(Continued)

OTHER PUBLICATIONS

PCT International Search Report and Written Opinion: PCT Application No. PCT/GB2012/051271; dated Aug. 31, 2012.

(Continued)

*Primary Examiner* — Jason-Dennis Stewart (57) ABSTRACT

An attachment mechanism, method of manufacture and method of use are described for releasably attaching a first component and a second component of an orthopaedic apparatus. The attachment mechanism comprises a boss extending from a surface of the first component, and having a free end and a side wall. A retaining mechanism is provided in the second component. The retaining mechanism comprises a plurality of walls defining an aperture in the second component to receive the boss therein. At least part of one of the plurality of walls is a resiliency flexible member engineered to apply sufficient force to a part of the side wall of the boss when inserted in the aperture to provide an interference fit between the boss and the plurality of walls of the aperture to releasably retain the boss within the aperture.

19 Claims, 7 Drawing Sheets

(56) References Cited

U.S. PATENT DOCUMENTS

| | | | |
|---|---|---|---|
| 5,197,488 | A | 3/1993 | Kovacevic |
| 5,387,241 | A | 2/1995 | Hayes |
| 5,470,354 | A | 11/1995 | Hershberger et al. |
| 5,472,415 | A | 12/1995 | King et al. |
| 5,683,469 | A | 11/1997 | Johnson et al. |
| 5,702,464 | A | 12/1997 | Lackey |
| 5,733,292 | A | 3/1998 | Gustilo et al. |
| 5,776,201 | A | 7/1998 | Colleran et al. |
| 5,928,286 | A | 7/1999 | Ashby et al. |
| 6,214,052 | B1 | 4/2001 | Burkinshaw |
| 6,673,114 | B2 | 1/2004 | Hartdegen et al. |
| 6,916,324 | B2 | 7/2005 | Sanford et al. |
| 7,105,026 | B2 | 9/2006 | Johnson et al. |
| 7,309,363 | B2 | 12/2007 | Dietz |
| 7,632,283 | B2 | 12/2009 | Heldreth |
| 7,632,314 | B2 | 12/2009 | Dietz |
| 8,236,004 | B2 * | 8/2012 | Jonas .................. A61F 2/4609 606/91 |
| 8,603,101 | B2 | 12/2013 | Claypool et al. |
| 8,617,250 | B2 | 12/2013 | Metzger |
| 8,951,301 | B2 | 2/2015 | Wogoman et al. |
| 8,968,412 | B2 | 3/2015 | Wogoman et al. |
| 2002/0082607 | A1 | 6/2002 | Heldreth et al. |
| 2004/0230315 | A1 | 11/2004 | Ek |
| 2006/0111726 | A1 * | 5/2006 | Felt .................... A61B 17/1659 606/86 R |
| 2006/0184176 | A1 | 8/2006 | Straszheim-Morley et al. |
| 2007/0156230 | A1 * | 7/2007 | Dugan ..................... A61F 2/91 623/1.16 |
| 2007/0239165 | A1 | 10/2007 | Amirouche |
| 2008/0091271 | A1 | 4/2008 | Bonitati |
| 2010/0010635 | A1 | 1/2010 | Straszheim-Morley et al. |
| 2010/0125337 | A1 | 5/2010 | Grecco et al. |
| 2010/0280616 | A1 * | 11/2010 | Frasier ..................... A61F 2/44 623/17.16 |
| 2010/0331954 | A1 * | 12/2010 | Sahatjian ................. A61F 2/88 623/1.11 |
| 2012/0089235 | A1 * | 4/2012 | Conway ............. A61B 17/8066 623/22.24 |
| 2012/0158152 | A1 | 6/2012 | Claypool et al. |
| 2013/0006252 | A1 | 1/2013 | Waite et al. |
| 2013/0006253 | A1 | 1/2013 | Waite et al. |
| 2013/0006370 | A1 | 1/2013 | Wogoman et al. |
| 2013/0006371 | A1 | 1/2013 | Wogoman et al. |
| 2013/0006376 | A1 | 1/2013 | Wogoman et al. |
| 2013/0006377 | A1 | 1/2013 | Waite et al. |
| 2013/0020733 | A1 | 1/2013 | Berger |
| 2013/0030538 | A1 | 1/2013 | Metzger et al. |
| 2013/0079671 | A1 | 3/2013 | Stein et al. |
| 2013/0103160 | A1 | 4/2013 | Young |
| 2013/0173011 | A1 | 7/2013 | Otto et al. |
| 2013/0204267 | A1 | 8/2013 | Dietz |
| 2013/0261505 | A1 | 10/2013 | Sherman et al. |
| 2013/0261758 | A1 | 10/2013 | Claypool et al. |
| 2013/0261759 | A1 | 10/2013 | Claypool et al. |
| 2014/0052269 | A1 | 2/2014 | Claypool et al. |

FOREIGN PATENT DOCUMENTS

| | | |
|---|---|---|
| EP | 1836997 A1 | 9/2007 |
| EP | 2168537 A1 | 3/2010 |
| EP | 2168537 B1 | 11/2011 |
| EP | 2540256 A1 | 1/2013 |
| WO | WO 9925263 A1 | 5/1999 |
| WO | WO 0013597 A1 | 3/2000 |
| WO | WO 03061522 A2 | 7/2003 |
| WO | WO 2008024836 A2 | 2/2008 |
| WO | WO 2008024836 A3 | 2/2008 |
| WO | WO 2008054389 A1 | 7/2008 |
| WO | WO 2011073632 A1 | 6/2011 |

OTHER PUBLICATIONS

UK Search Report: GB 1114059.7; dated Dec. 7, 2011.
Coordinate Ultra Revision Knee System, Surgical Technique, 1997, p. 24.
GMK Revision, Surgical Technique, Ref. 99.27.12US Rev.1,1999, 74 pages.
P.F.C. Sigma Knee System, Revision, Surgical Technique, 2000 p. 66.
P.F.C. Sigma Rotating Platform Knee System with M.B.T. Tray, Primary Procedure and a Curved or Posterior Stabilized Implant, 2003, 43 pages.
Smith & Nephew, Legion, Revision Knee System, Surgical Technique, 2005, 40 pages.
PFC Sigma RP-F, Specialist 2 Instruments, Surgical Technique, Performance in Flexion, 2007, 32 pages.
Sigma High Performance Instruments, Design Rationale, 2007, 12 pages.
Biomet, Vanguard SSK, Revision System, Surgical Technique, Feb. 2008, 64 pages.
LCS High Performance Instruments, Surgical Technique, 2008, 44 pages.
DePuy Orthopaedics, Inc., Sigma Revision and M.B.T. Revision Tray, Surgical Technique, 2008, 82 pages.
Zimmer NexGen LCCK, Surgical Technique for use with LCCK 4-in-1 Instrument, 2009, 52 pages.
Sigma High Performance Instruments, Classic Surgical Technique, 2010, 52 pages.
Sigma Revision and M.B.T. Revision Tray, Surgical Technique, 2012, p. 84.
S-Rom Noiles Rotating Hinge, Surgical Technique, 2012, p. 76.
Declaration of Thomas E. Wogoman (with Exhibits A-J), executed Mar. 22, 2015, 157 pages from U.S. Pat. No. 9,132,011.

* cited by examiner

ATTACHMENT MECHANISM

CROSS REFERENCE TO RELATED APPLICATION

This application is a National Stage 35 U.S.C. 371 of International Patent Application PCT/GB2012/051271 filed Jun. 6, 2012, which claims priority to United Kingdom Patent Application GB1114059.7, filed Aug. 16, 2011 (now abandoned).

BACKGROUND OF THE INVENTION

The present invention relates to an attachment mechanism and in particular a mechanism for releasably attaching two or more parts of surgical apparatus.

There are a large number of times when it may be desirable to temporarily attach two parts of a surgical apparatus together. For example, one part may be universal while another part may be patient or procedure specific or otherwise need to be varied depending on circumstance during an operation. The parts should be attachable with sufficient reliability that they will not come apart during normal use, so that the surgeon does not need to use one or more hands to keep the parts together, while being easily detachable so that time is not wasted during surgery manipulating or otherwise handling complex or fiddly attachment mechanisms.

It is also beneficial if such attachment mechanisms are simple to manufacture, clean after use and are useable with a wide variety of instruments, devices, parts, tools or other surgical devices.

One example of a releasable attachment mechanism is a bayonet type fastening as used to releasably attach markers to bone pins to allowing tracking of bones using various optical tracking systems. However, they are not entirely easy to handle, for example when wet or when wearing surgical gloves, and include multiple moving parts and so are complicated to manufacture and can trap debris making them harder to clean.

Releasable attachment mechanisms can also be used in connection with implant trial components. For example, prosthetic knee joints can include multiple parts which engage and articulate against each other via articulating surfaces, e.g., the condyles of a prosthetic femoral component and the articulating surface of a tibial component. During a surgical procedure, a surgeon often makes a number of bone cuts to prepare the surgical site to accept the prosthetic components. During a trialing stage, the surgeon may place a number of trail components within the surgical site to determine the appropriate dimensions, e.g. size, of the actual prosthetic components to be used to replace the joint. The actual prosthetic components themselves are not used, in order to prevent them being damaged and in case the surgeon selects an inappropriately sized component initially.

One example of the use of trial components, in a knee procedure, is to use a trial tibial component, such as a tibial tray, which includes a tibial articular surface. Various different sized trial components, in the medial-lateral direction, can be used depending on the size of the resected tibial surface. Depending on the height of the tibial cut, and also the femoral component and its position on the femur owing to the femoral cuts, the gap in the knee joint may vary. Also, the size of the gap in the knee joint may vary owing to soft tissue issues such as owing to the ligaments. In order to modify the gap between the tibial and femoral components, one or more shims of different thicknesses may be placed between an underside of the tibial tray and the resected tibial surface in order to reduce the gap between the tibial component and the femoral component.

However, there are difficulties in handling the tibial tray and shims in the operating theatre environment. Bodily fluids and debris from the surgical site can make the handling and manipulation of the tray and/or shims difficult. Further, articulation of the joint with the trial in place, for example to measure the gap in flexion and extension, places the joint components under various forces which could dislodge the trial components.

It would therefore be beneficial to provide a simple and easy to use mechanism to improve the ease and reliability of releasably attaching parts of an orthopaedic apparatus, particularly during a surgical procedure.

BRIEF SUMMARY OF THE INVENTION.

A first aspect of the invention provides an attachment mechanism for releasably attaching a first component and a second component of an orthopaedic apparatus, the attachment mechanism comprising: a boss extending from the first component and a retaining mechanism provided in the second component. The retaining mechanism comprises a plurality of walls defining an aperture in the second component to receive the boss therein. At least part of one of the plurality of walls can be a resiliently flexible member engineered to apply sufficient force to a part of the boss when inserted in the aperture to provide an interference fit between the boss and at least one of the plurality of walls to releasably retain the boss within the aperture.

By providing a part of one of the walls defining the aperture in which the boss can be received as a resiliently flexible member, a simple to operate attachment mechanism can be provided which is easy to manufacture and has few parts.

The attachment mechanism can comprise a plurality of bosses and a plurality of retaining mechanisms. A separate or different retaining mechanism can be provided for each boss.

The retaining mechanism can have a unitary construction. The walls can be provided as integral parts of the second component and so no secondary or ancillary separate parts are needed to provide the releasably attachment mechanism.

One, a plurality or all of the plurality of walls can include one or a plurality of parts each being a resiliently flexible member. A part of one, a plurality or all of the walls can be provided as a resiliently flexible member. The whole of one, a plurality or all of the walls can be provided as a resiliently flexible member. A plurality of parts of one, a plurality or all of the walls can be provided as a resiliently flexible member.

The or each resiliently flexible member can be engineered to be resiliently flexible in a number of different modes of flexibility. Preferably, the or each resiliently flexible member is resiliently bendable.

A cavity or cavities can be located in the second component adjacent the or each resiliently flexible member. The cavity can be located on a side of the or each resiliently flexible member opposite the aperture. The cavity preferably extends through the entire thickness of the second component.

A pair of resiliently flexible members can be provided on opposed sides of the aperture.

The or each resiliently flexible member can comprise an entire one of the plurality of walls. That is the entire wall can be resiliently flexible, rather than just a part of the wall.

The boss can haves a body and a tip. The tip of the boss can have a smaller lateral dimension than the body. The body can have a substantially constant lateral dimension, i.e. the body may not be tapered. The tip may be tapered or otherwise have a smaller lateral dimension than the body. For example, the tip may have a chamfer extending at least partially or wholly around its rim.

The boss can be cylindrical, and in particular right cylindrical. The boss can be a circular, curved or curvi-linerar or polyhedral cylinder.

The boss can be partially or wholly tapered. The boss can have a draft angle. Preferably the draft angle is in the range of from about 0.5 degrees to about 5 degrees.

The resiliently flexible member can have two or more parts. Each part can have a free end. The free ends can define a gap therebetween. The gap can be at various positions along the wall, including the middle of the wall, one third along or one quarter along the length of the wall.

The aperture can have a dimension greater than the largest lateral dimension of the boss. The resiliently flexible member can extend along the length of the dimension. This can help to reduce the stiffness of the resiliently flexible member.

At least one of the plurality of walls defining the aperture can include one or more retaining formations extending into the aperture. The retaining formation or formations can co-operate with another of the plurality of walls, or another retaining formation, to retain the position of the boss in the aperture. The retaining formation and wall or retaining formations can define a dimension of the aperture substantially matching a lateral dimension of the boss so as to prevent the boss sliding laterally with the aperture when received therein.

The resiliently flexible member can have a composite construction. The or each resiliently flexible member can include, or consist of, a material different to the material from which the rest of the retaining mechanism is made. The resiliently flexible member can include, or consist of, a metal part or parts. The rest of the retaining mechanism can be made of a plastic. The metal part or parts can be encased by a plastics material of the remainder of the retaining mechanism. The different material can be a different type of plastic to a plastic of which the rest of the retaining mechanism is made.

The second component can be formed entirely of a single piece of material. This facilitates manufacture of the second component as the retaining formation is formed wholly from the same material as the second component, rather than having a compound construction.

The boss and/or retaining formation can be formed from a plastics material.

A further aspect of the invention provides an orthopaedic apparatus, comprising: a first component; a second component; and an attachment mechanism according to the preceding aspects of the invention to releasably attach the first and second components.

The attachment mechanism can have any of the preferred features of the first aspect of the invention.

The orthopaedic apparatus can have a plurality of attachment mechanisms according to the first aspect of the invention, and preferably at least two attachment mechanisms.

The first component and/or the second component can be a trial component.

The trial component can be a tibial component and/or the other component can be a shim or spacer component.

The apparatus can further include a third component. The third component can be a further shim. The further shim can have a different thickness to the shim and the further shim can include a further retaining mechanism.

The orthopaedic apparatus can be an instrument. The first component can be a part of the instrument and/or the second component can be a part of the instrument. The first or second component can be or include a handle and/or the other of the first and second part can be a working part of the instrument.

The first component or second component can be an orthopaedic instrument and the other of the first and second component can be an accessory. The accessory can be a trackable marker.

A further aspect of the invention provides a method of manufacturing an orthopaedic apparatus having a first component and a second component which are releasably attachable to each other. The method can comprise forming the first component with a boss extending from a surface of the first component and forming the second component with a retaining formation comprising a plurality of walls defining an aperture to receive the boss therein. At least part of one of the plurality of walls can be a resiliently flexible member engineered to apply sufficient force to a part of the side wall of the boss when inserted in the aperture to provide an interference fit between the boss and at least one of the plurality of walls of the aperture to releasably retain the boss within the aperture.

The first component and/or the second component can be formed by molding or machining. The first and/or second material can be molded or machined from a plastics material.

The first component and/or the second component can be formed by stamping, forging, casting or printing. For example, selective laser sintering (SLS) can be used as a form or printing for metals.

Forming the second component can include molding the plastics material over at least one metal member to form the or each resiliently flexible member.

The first component and/or the second component can be formed entirely from plastic.

The first component and/or the second component can be formed entirely as a unitary part. That is, the first component and/or second component can be manufactured with the boss and/or retaining formation as integral parts.

A further aspect of the invention provides a method for assembling an orthopaedic apparatus from at least a first component and a second component. A free end of a boss extending from a surface of the first component can be positioned adjacent an aperture of a retaining formation of a second component. The boss can be pushed into the aperture, whereby a resiliently flexible member applies sufficient force to a part of a side wall of the boss to provide an interference fit between the boss and at least one wall of the aperture to releasably retain the boss within the aperture.

BRIEF DESCRIPTION OF THE DRAWINGS

Embodiments of the invention will now be described in detail, by way of example only, and with reference to the accompanying drawings, in which.

Similar items in different Figures share common reference numerals unless indicated otherwise.

DETAILED DESCRIPTION OF THE INVENTION

Embodiments of the invention will now be described with reference to use of the invention as part of a tibial trial and shim assembly and an introducer instrument. However, it will be appreciated that the attachment mechanism of the invention can be used for releasably attaching components of other orthopaedic apparatus where it is desirable to temporarily attach the components, for example for ease of handling, and then releasing the components.

Figure 1:
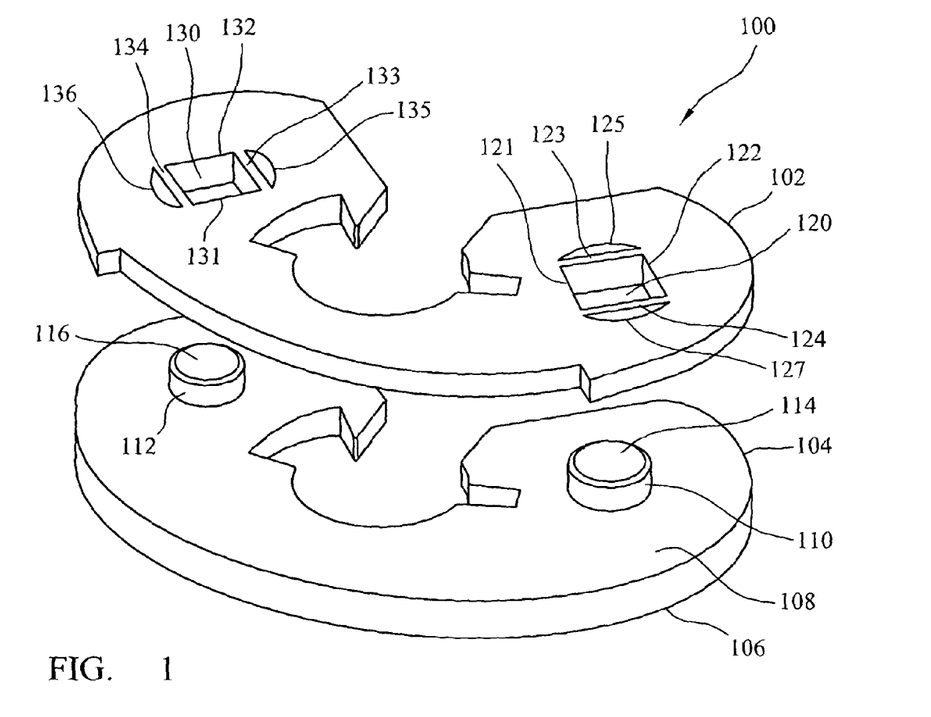
FIG. 1 shows a perspective view of a trial and first shim assembly in a detached state according to the invention and including an attachment mechanism according to the invention.
Figure 2:
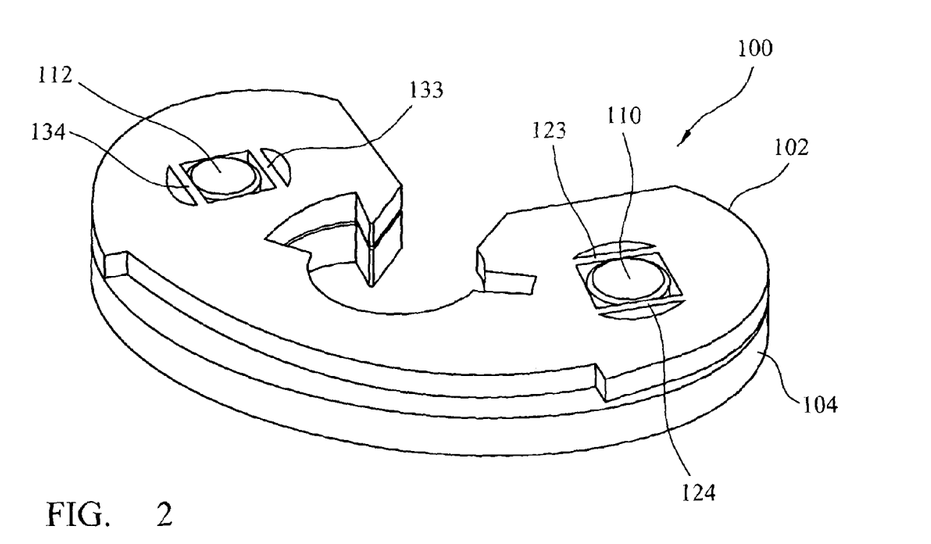
FIG. 2 shows a perspective view of the trial and first shim assembly in an attached state.

With reference to FIGS. 1 and 2 there are shown perspective drawings of a first embodiment of an orthopaedic assembly 100 comprising a shim component 102 and a tibial component 104. FIG. 1 shows the shim 102 and tibial 104 components in a detached state. FIG. 2 shows the shim 102 and tibial 104 components in a releasably attached state.

The tibial component 104 has a generally curved or crescent shape and is generally planar. The tibial component 104 has an articulating surface 106 on a first side for receiving the condylar parts of a femoral prosthetic component in use. The articulating surface is provided as an integral part of tibial component 104. In an alternative embodiment, a separate articulating surface component can be provided which is releasably attachable to component 104 via surface 106 and the separate articulating surface component bears the articulating surface. An opposed second side 108 presents a generally flat surface. A first boss 110 extends from the second surface 108 toward a first end and a second boss 112 extends from the second surface 108 toward a second end of the tibial component 104. Each boss is in the form of a generally right circular cylinder. The rim of the free end of each boss includes a chamfered portion 114, 116. Hence, the tip of each boss has a slightly smaller lateral dimension (in this case radius) than the lateral dimension of the main body of the boss. The main body of each boss has a side wall.

The tibial trial component 104 and the shim component 102 are each made entirely from a single piece of plastics material, such as glass reinforced polyarylamide, polyphenylsulphone (PPSU), polyetherimide (PEI), acrylonitirde (ABS) or similar. The components can be can be formed by injection molding using such plastics materials. The components can also be formed by machining such plastic materials, or a combination of molding and machining.

The shim component 102 also has a generally curved or crescent shape and is generally planar. The shim component 102 has similar dimensions to the tibial component 104. The shim component has a first aperture 120 therein toward a first end and a second aperture 130 therein toward a second end. The first and second apertures are at locations in the shim generally in registration with the locations of the respective bosses 110, 112 when the shim component and tibial component are in registration, as best shown in FIG. 2. Aperture 120 is defined by walls 121, 122, 123 and 124. Opposed walls 121 and 122 are entirely rigid. The dimension of aperture 120 between walls 121 and 122 is substantially the same as the diameter of the body of boss 110 such that boss 110 can be received snugly therein. The side walls defining the aperture are in clearance to negate positional tolerances.

Each of walls 123, 124 is engineered to be resiliently flexible by bending. The actual material of the flexible walls 123, 124 themselves is substantially rigid as they are made from the same material as the remainder of the shim component which is itself rigid. This is preferred compared to other approaches, as the entire component can be made from the same material rather than having to use different materials with different properties for the main body of the component and the interference fit components of the retaining formation. In the invention, the flexible walls are engineered to allow them to flex by bending and are resilient so that they try to adopt their original position when flexed out of position, within their elastic limit. A first circular segment shaped cavity 125 is provided adjacent wall 123 and on an opposite side to the aperture 120. A similar second circular segment shaped cavity 127 is provided adjacent wall 124 and on an opposite side to the aperture 120. Cavities 125 and 127 allow walls 123 and 124 to flex inwardly, that is away from aperture 120, in use as will be described in greater detail below. The dimension of aperture 120 between walls 123 and 124 is slightly less than the diameter of the body of boss 110.

The resiliently flexible walls 123, 124 and main aperture 120 provide a retaining mechanism for releasably retaining boss 110 in use.

A second retaining mechanism is provided by the second cavity 130 which is defined similarly to first aperture 120. The second aperture 130 is defined by walls 131, 132, 133 and 134. Walls 131 and 132 are entirely rigid and the second aperture 130 has a dimension between these walls substantially the same as the diameter of the body of the second boss 112 such that it can be snugly received therebetween. Walls 133 and 134 are resiliently flexible and the dimension of the aperture 130 between them is slightly smaller than the diameter of the body of boss 112. A respective circular segment shaped cavity 135, 136 is provided adjacent each of walls 133, 134 on a side opposite to the second aperture 130. Cavities 135, 136 pass through the entire thickness of the shim 102.

In order to releasably attach the shim 102 to the tibial component 104, the free end of each boss 110, 112 is each introduced into a respective one of the apertures 120, 130. The chamfered edge of the free end of the bosses facilitate the introduction of the tip of each boss into the aperture as the tip of each boss has a slightly smaller dimension than the lateral dimensions of the apertures. As the free ends of the bosses are introduced into the apertures, the flexible walls 123, 124 and 133, 134 each bend outwardly (away from their respective apertures) in order to accommodate the body of each respective boss. The shim 102 and tibial component 104 are pressed together until they have adopted the attached configuration illustrated in FIG. 2. As the separation between the pairs of flexible walls 123, 124 and 133, 134 is slightly less than the diameter of the body of each boss, and as the walls are resilient, the walls are urged against the side walls of the bosses so as to generate an interference fit with sufficient force to prevent the shim component from detaching from the tibial component.

Hence, in use, a surgeon can temporarily attach a shim 102 to the articular component 104 using the attachment mechanism provided by the boss and retaining mechanism combinations.

Figure 3:
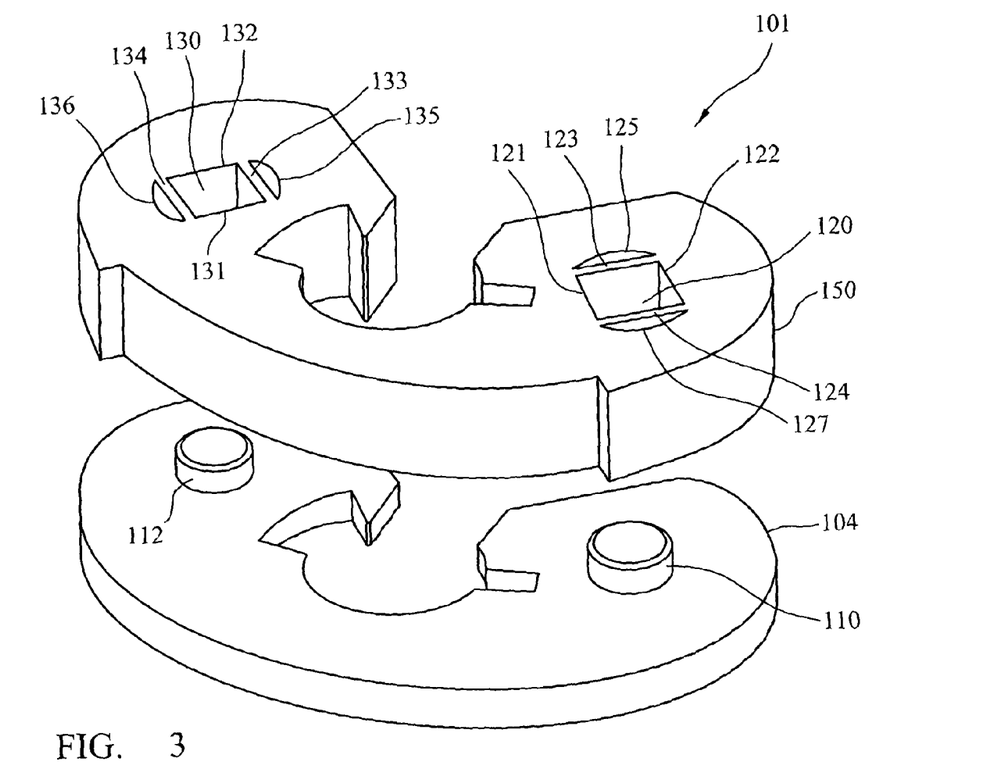
FIG. 3 shows a perspective view of a trial and second shim assembly in a detached state.
Figure 4:
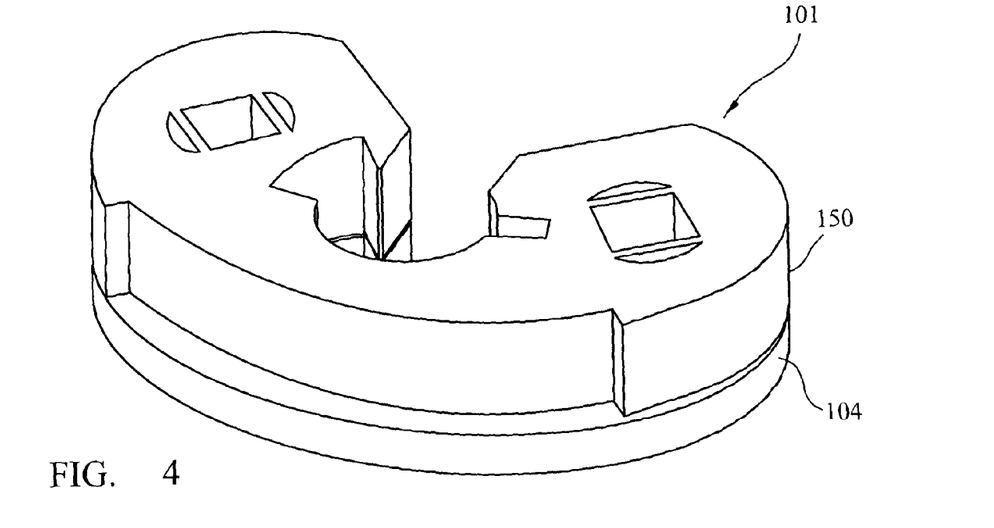
FIG. 4 shows a perspective view of the trial and second shim assembly in an attached state.

FIGS. 3 and 4 show perspective views of an assembly 101 similar to assembly 100 but in which the shim component 150 has a greater thickness than the shim component 102 shown in FIGS. 1 and 2. Other than the thickness of shim component 150, the shim component 150 is substantially identical to shim component 102. Further shims each having different thicknesses to the other shims can of course be provided.

Continuing description of use of the invention, if it is determined that the tibial-femoral gap is too large with the first shim 102 in place, then the surgeon may remove the first shim 102 from the tibial trial component 104 by simply pulling to detach the shim component 102 from the tibial component 104. The surgeon can then attach the second, thicker shim, 150 to the same tibial component 104. Similarly to the first shim, the second shim 150 includes a retaining mechanism provided by the apertures and resiliently flexible walls which releasably retain the respective bosses 112, 110 therein when the free ends of bosses 110, 112 are introduced into respective apertures 120, 130 and the shim component 150 and tibial component 104 are pressed together. The resiliently flexible walls 123, 124 and 134, 133 are engineered to flex by bending and their resilient nature causes them to be urged against the walls of the bosses 112, 110 so as to create an interference fit to releasably attach the shim and tibial component in the attached configuration illustrated in FIG. 4.

There are a number of benefits to the attachment mechanism of the present invention. The attachment mechanism is less susceptible to the effects of manufacturing variation than previous attachment mechanisms. The attachment mechanism does not require high precision or high tolerance manufacturing methods to be used as it relies on a more gross engineering property, being the resiliently deformable walls. The detachment mechanism is simple and involves no further ancillary or additional components. This reduces the cost of manufacture, increases the simplicity of operation, improves cleanability of the component and provides increased ease of manufacture. Both the tibial trial component and shim components can be easily manufactured using a two piece mould. Once the tooling has been produced, there is no further additional cost associated with its use. The attachment mechanism can be used in single use disposable products, but it can also be used on re-usable products which also require a releasable attachment mechanism.

The shims and/or tibial components can be made from various plastics materials, as described above and the shims and/or articular components can be made by an injection moulding process in which the injection mould tool is used to define the main cavities and circular segment cavities defining the retaining mechanism. Hence, it will be appreciated that both the tibial component and shim component can be made entirely from a single piece of material and do not have any ancillary or subsidiary parts. This greatly improves ease of manufacture. Also, the trial and shims can be provided as single use disposable components.

In alternative embodiments, the trial and shim components can be made from a suitable metal, such as surgical grade stainless steel, and can be formed by machining or casting, for example.

In other embodiments, as described below, the components can have a compound construction in which they are made from plastics and metal parts or from combinations of different types of plastics, such as a hard plastic for the retaining formation and a softer plastic for the resiliently deformable walls.

It will be appreciated that the exact interference fit, and strength thereof, between the flexible walls and the bosses can be optimised to provide a desired holding force. A number of properties of the retaining mechanism and/or boss can be varied depending on the retaining force required. For example, features of the resiliently flexible member can be varied. For instance, the material, length, depth, thickness and extent of interference fit of the flexible walls can be varied. The orientation of the walls can be varied. The number of flexible walls can be varied. The amount, or number of parts, of each wall which is flexible can be varied. The shape and positioning of the cavities adjacent the walls can be varied. The cross sectional shape of the resiliently flexible members can also be varied. Some of these variations are illustrated in FIGS. 5 to 7, which are merely by way of non-limiting example only.

Figure 5:
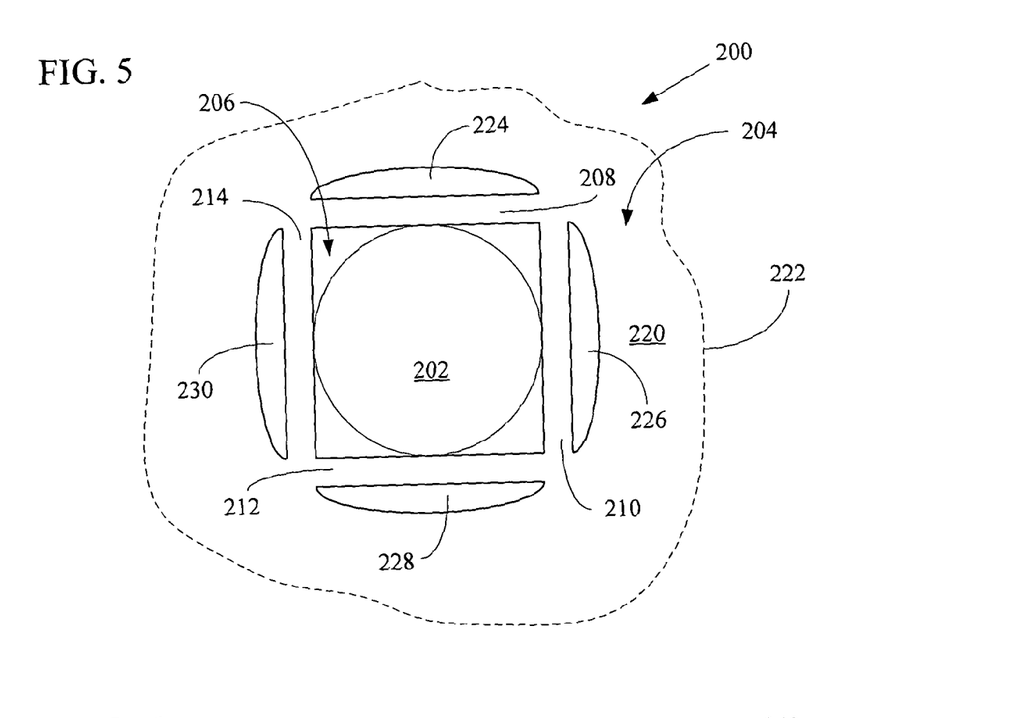
FIG. 5 shows a schematic plan view of a further attachment mechanism according to the invention.

FIG. 5 shows a plan view of a second embodiment of the attachment mechanism in the attached configuration. The attachment mechanism 200 includes a right circular cylindrical boss 202 and a retaining mechanism 204 provided by a cavity 206 defined by four resiliently flexible walls 208, 210, 212, 214 all provided as a part of a shim component 220, as illustrated by dashed line 222. The second embodiment of the attachment mechanism is similar to the attachment mechanism of the first embodiment other than there being four resiliently flexible walls, each of which has a generally circular segment shaped cavity 224, 226, 228, 230 associated with it. Also, the separation between each pair of walls, in the un-flexed state, is slightly less than the diameter of the boss such that when the boss 202 is inserted within the aperture 206, the walls are caused to bend with their resilient nature imparting the interference fit by interaction with the wall of the boss 202.

Figure 6:
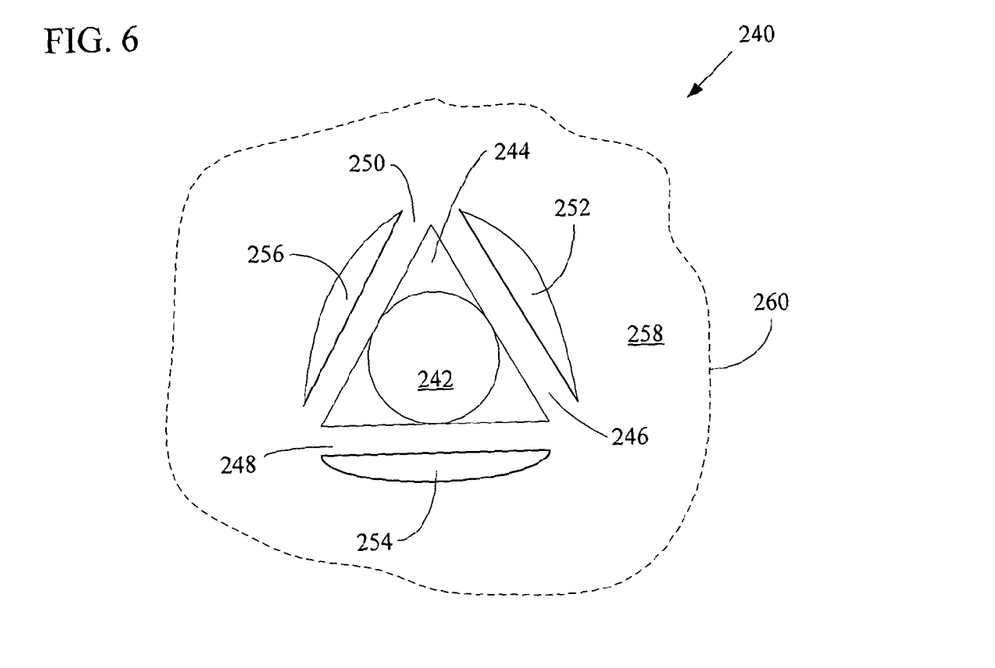
FIG. 6 shows a schematic plan view of a further attachment mechanism according to the invention.

FIG. 6 shows a plan view of a third embodiment 240 of the attachment mechanism of the invention. In this third embodiment, a right circular cylindrical boss 242 is provided and a retaining mechanism is provided by triangular aperture 244 defined by three resiliently flexible walls 246, 248, 250. Each wall has a cavity 252, 254, 256 associated with it on an opposite side to the main aperture 244. The retaining mechanism is provided in a part of shim component 258 as illustrated by dashed line 260.

Figure 7:
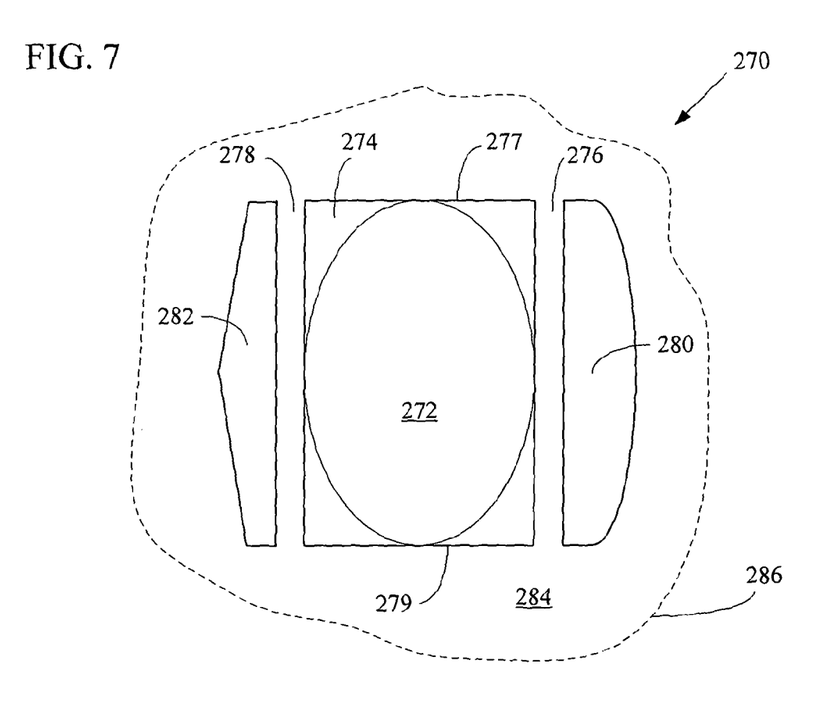
FIG. 7 shows a schematic plan view of a further attachment mechanism according to the invention.

FIG. 7 shows a plan view of a fourth embodiment 270 of an attachment mechanism according to the invention. The attachment mechanism includes an oval cylindrical boss 272 and a retaining mechanism provided by rectangular aperture 274 defined by first and second opposed resiliently flexible walls 276, 278 and rigid walls 277, 279. First flexible wall 276 has a cavity 280 associated with it on a side opposite to the main aperture 274. Second resiliently flexible wall 278 has a second cavity 282 associated with it and located on the side opposite to the main aperture 274. As illustrated in FIG. 7, first cavity 280 and second cavity 282 have different shapes. First cavity 280 has a partially linear, partially curved shape. Second cavity 282 has a polyhedral shape defined by straight wall segments. Different shaped cavities may be chosen to engineer specific bending properties and resiliencies of the associated wall. Alternatively, different cavity shapes may be selected for ease of manufacture.

Figure 8:
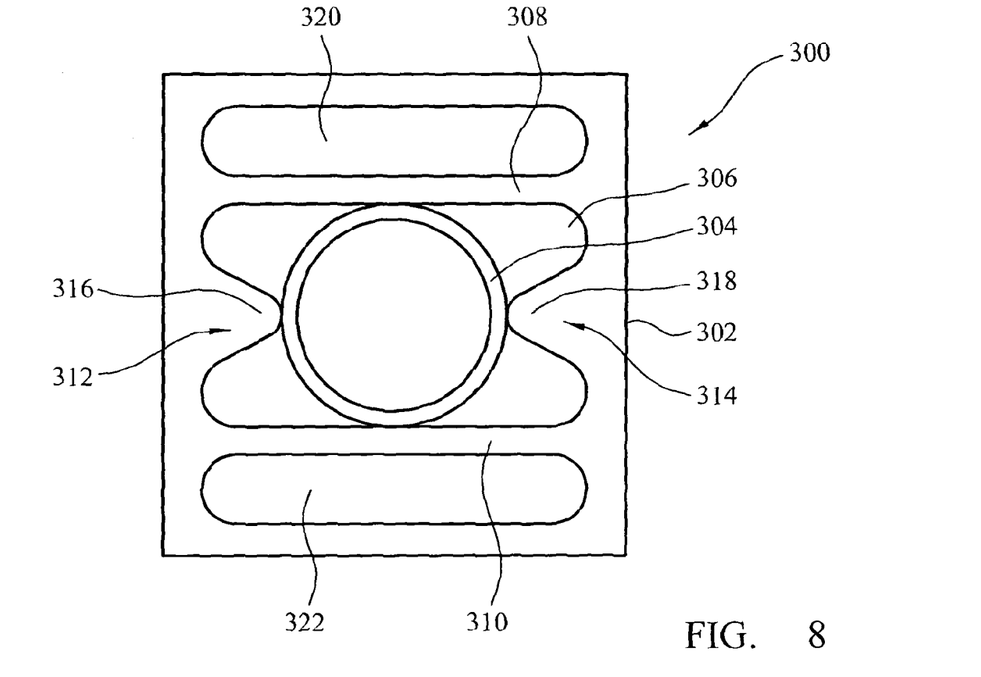
FIG. 8 shows a schematic plan view of a further attachment mechanism according to the invention.

With reference to FIG. 8, there is shown a further embodiment of an attachment mechanism 300 according to the invention. The attachment mechanism 300 also includes a retaining formation 302 and a boss 304 similar to that described previously. Retaining formation 302 includes a plurality of walls defining an aperture 306 therein. A first pair of walls 308, 310 are provided on opposed sides of aperture 306 and are in the form of resiliently flexible beams. Opposed end walls 312, 314 each include a retaining formation 316, 318 which extend inwardly toward the aperture 306. Aperture 306 has a dimension in a lateral direction, generally parallel towards 308 and 310 which is greater than the dimension of the aperture in a perpendicular transverse direction. The dimension of the aperture in the transverse direction is slightly smaller than the diameter of the body of boss 304 such that walls 308 and 310 exert a reactive force against the walls of the boss to provide an interference fit. The separation between the ends of retaining formations 316 and 318 is slightly larger than the diameter of boss 304 and the retaining formations act to prevent the boss sliding within aperture 306.

By providing the aperture with a greater lateral dimension than the diameter of the boss, the length of the resiliently flexible wall members 308, 310 can be made larger so as to allow the exact thickness of the interference fit to be optimised for the specific application. In this instance, increasing the length of the resiliently flexible beams 308, 310 acts to reduce their stiffness and therefore reduce the retaining force. As in the other embodiments, cavities 320 and 322 are provided on the side of the walls 308, 310 opposed to the aperture.

Figure 9:
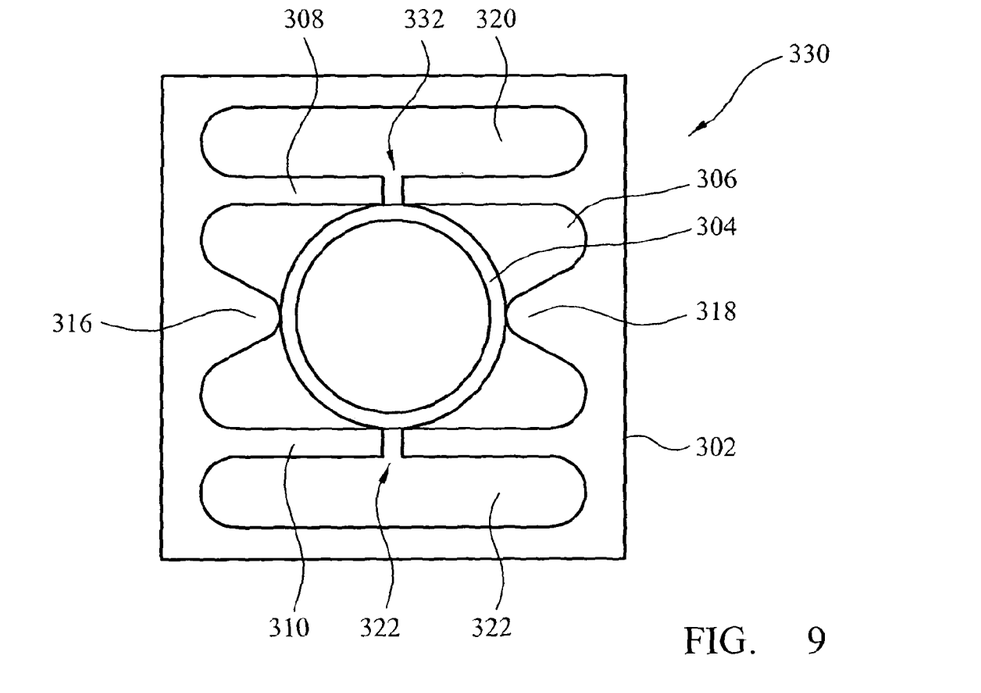
FIG. 9 shows a schematic plan view of a further attachment mechanism according to the invention.

FIG. 9 shows a further embodiment of the attachment mechanism 330 according to the invention. This further embodiment is similar to the embodiment 300 shown in FIG. 8. However, this further embodiment 330 illustrates another way in which the resiliently flexible member can be engineered in order to modify the retaining force of the attachment mechanism 330. In this embodiment, the walls providing the resiliently flexible members 308, 310 are each split in half. That is, there is a gap 332, 334 in each wall at the mid-point of each wall. Each wall 308, 310 comprises first and second wall parts extending from the retaining mechanism and with a free end at the middle of the wall. By providing the split in the walls, the stiffness of the beams can again be decreased in order to optimise the holding force provided by the attachment mechanism for its specific application. Each part of the wall acts generally like a leaf spring. It will be appreciated that the split can be provided at different positions along the length of the wall again in order to modify the retaining force provided.

Figure 10:
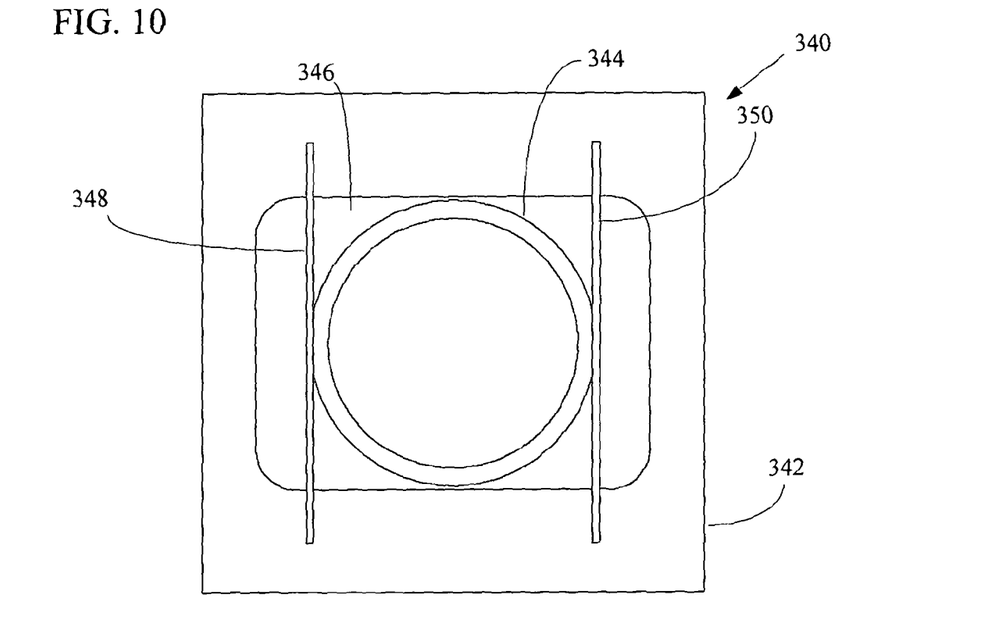
FIG. 10 shows a schematic plan view of a further attachment mechanism according to the invention.
Figure 11:
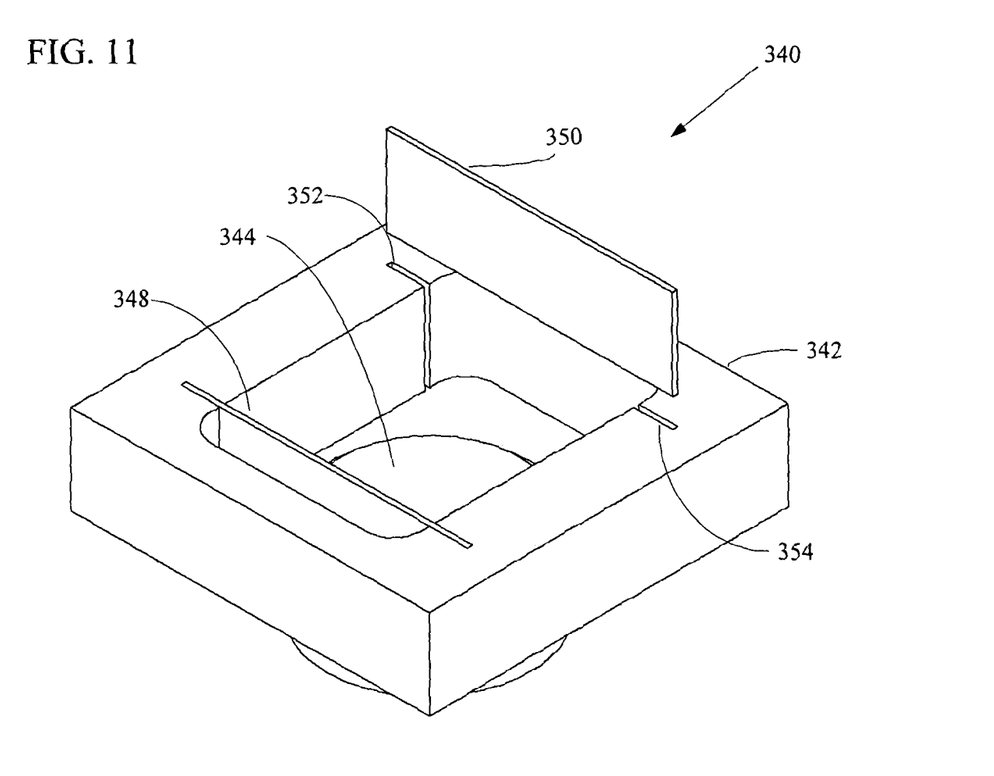
FIG. 11 shows a perspective view of the attachment mechanism shown in FIG. 10 in a partially disassembled state.

With reference to FIGS. 10 and 11, there are shown plan perspective views of a further embodiment of an attachment mechanism 340 according to the invention. The retaining mechanism is similar to those described previously and includes a retaining formation 342 and boss 344. The retaining formation includes an aperture 346 defined by internal walls of the retaining formation. However, in this embodiment, a pair of opposed walls 348, 350 which provide resiliently flexible beams, are in the form of thin metal plates which are received in notches, e.g. 352, 354 in the main body of the retaining formation. Hence, in this embodiment 340, the retaining formation has a compound structure, i.e. is not made from the same single material or with a single unitary element. Rather, the walls 350, 348 are made from a different material to the boss and remainder of the retaining formation 342 which are made of a plastics material. Hence, the material of the resiliently flexible walls 348, 350 and their dimensions can be selected in order to optimise the retaining force provided by the attachment mechanism.

In other embodiments, the resiliently flexible walls 348, 350 can be made from materials other than metal, such as plastics materials. The plastics material used for the resiliently flexible walls 348, 350 can be different to the plastics material used to make the remainder of the retaining formation. In yet further embodiments a compound retaining formation can be provided in which metal, or other material, plates are used to provide the resiliently flexible walls, but the wall elements are over moulded by plastics material during formation of the retaining formation so as to be wholly enclosed. Hence, strips or sections of metal, or other material, can be encased within the plastics material so as to provide an optimised degree of resilience. The metal wall elements can be made from a variety of metals and alloys, including, for example stainless steel, titanium alloy (e.g. Ti6Al4V) and Nitinol.

Figure 12:
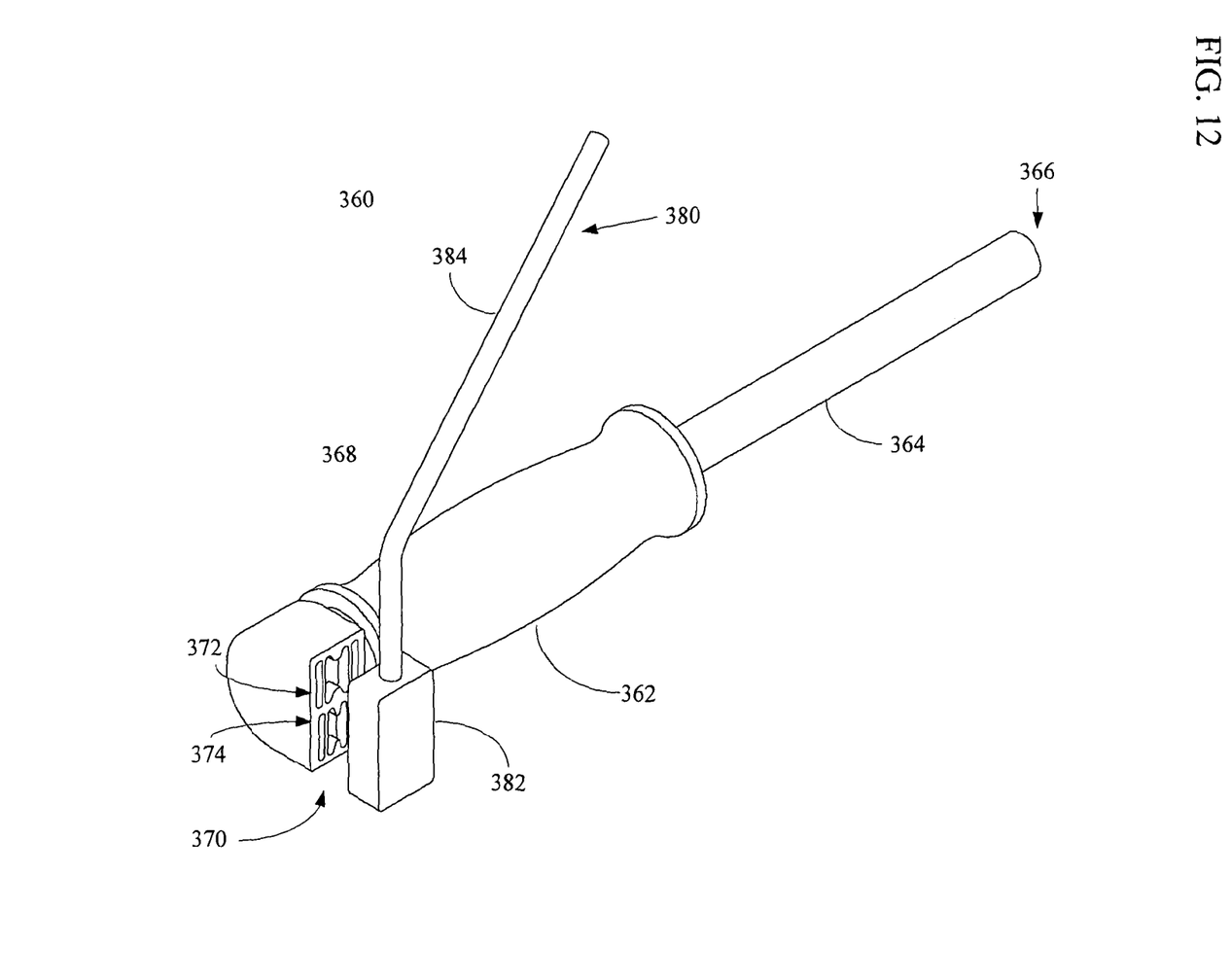
FIG. 12 shows a perspective view of an instrument according to the invention and including an attachment mechanism according to the invention.

FIG. 12 shows a schematic perspective view of an instrument 360 according to the invention, including an attachment mechanism 370 according to an embodiment of the invention. Instrument 360 includes a handle 362 and a shaft 364 with a free end 366 to which a working part may be attached. For example, instrument 360 can be an acetabular cup inserter and a trial or acetabular cup prosthesis may be attached to free end 366 for delivery into the acetabular of a patient. A proximal end 368 at an opposite end to free end 366 of the instrument bears an attachment mechanism 370 according to the invention. The attachment mechanism includes a pair of retaining formations 372, 374 similar to embodiment 300 shown in FIG. 8. An accessory 380 of the instrument includes a foot part 382 bearing a pair of bosses (not visible in FIG. 12). Accessory 380 includes an arm 384 extending from the foot 382 to which a star array trackable by an optical tracking system can be attached. Hence, accessory 380 may be releasably attached to the cup inserter instrument when the cup inserter is to be tracked during a computer aided surgery type procedure. Hence, if the cup inserter is not to be used in a tracked procedure, the accessory 380 can be removed from the cup inserter instrument to prevent impingement with other elements in the surgical field. However, when the cup inserter is to be tracked, the accessory 380 can be easily attached to the proximal end of the inserter instrument by engaging the pair of bosses in the retaining formations 372, 374.

It will be appreciated that the invention is not limited to releasably attaching marker arrays to the specific instrument. Rather, the attachment mechanism of the invention has a wide field of applicability to orthopaedic instruments. Further, the invention is not limited to attaching accessories to an instrument. The invention may also be used to attach parts of instruments to each other. For example, a handle part of an instrument may be universal and different types, sizes or shapes of working parts may be releasably attached to a universal handle part by using the attachment mechanism of the invention as an interface between the universal handle and different working parts.

By way of non-limiting examples, the attachment mechanism can be used to attach a guidance instrument or alignment guide to a broach handle, to aid correct broach alignment. The attachment mechanism can also be used to attach an alignment guide to an acetabular reamer, a drill, a trial inserter or implant inserter (as illustrated in FIG. 12) to aid correct acetabular component placement.

It will be appreciated that there are a wide number of variations to the shape, number, arrangement and positioning of the resiliently flexible members. Similarly, the shape, size and positioning of the boss can also be varied. The attachment mechanisms illustrated in the Figures and the orthopaedic apparatus in which they are used are intended to be by way of example only, and as illustration of some of the ways in which the attachment mechanism can be varied while still falling within the scope of the invention. Other variations and apparatus will be apparent to a person of ordinary skill in the art in view of the teaching herein.

The invention claimed is:

1. An attachment mechanism for releasably attaching a first component and a second component of an orthopaedic apparatus, the attachment mechanism comprising:
   a boss extending from a surface of the first component, the boss having a free end, and a non-threaded side wall extending from the free end to the surface of the first component;
   a plurality of non-threaded walls defining an aperture in the second component to receive the boss therein, wherein at least part of one of the plurality of walls is a resiliently flexible member shaped and configured to apply sufficient force to a part of the side wall of the boss when inserted in the aperture to provide an interference fit between the boss and the plurality of walls of the aperture to releasably retain the boss within the aperture wherein the components can be selectively and temporarily assembled by inserting the boss into the aperture of the second component and pressing the components together, and wherein the assembled first and second components can be disassembled by pulling to detach the components from one another.

2. The attachment mechanism of claim 1, wherein the plurality of walls includes a plurality of parts each being a resiliently flexible member.

3. The attachment mechanism of claim 2, wherein a pair of resiliently flexible members are provided on opposed sides of the aperture.

4. The attachment mechanism of claim 1, wherein the resiliently flexible member is engineered to be resiliently bendable.

5. The attachment mechanism of claim 1, wherein a cavity is located in the second component on a side of the resiliently flexible member opposite the aperture.

6. The attachment mechanism of claim 1, wherein the or each resiliently flexible member comprises an entire one of the plurality of walls.

7. The attachment mechanism of claim 1, wherein the boss has a body and a tip and wherein the tip of the boss has a smaller lateral dimension than the body.

8. The attachment mechanism of claim 1, wherein the boss is cylindrical.

9. The attachment mechanism of claim 1, wherein the resiliently flexible member has two parts.

10. The attachment mechanism of claim 9, wherein each part has a free end and the free ends define a gap therebetween and wherein the gap is at the middle of the wall.

11. The attachment mechanism of claim 1, wherein the aperture has a dimension greater than the largest lateral dimension of the boss and wherein resiliently flexible member extends along the length of the dimension.

12. The attachment mechanism of claim 11, wherein at least one of the plurality of walls defining the aperture includes a retaining formation extending into the aperture and which co-operates with another of the plurality of walls defining the aperture to define a dimension of the aperture substantially matching a lateral dimension of the boss so as to prevent the boss sliding laterally with the aperture when received therein.

13. The attachment mechanism of claim 1, wherein the resiliently flexible member includesa material different to the material from which the rest of the second component is made.

14. The attachment mechanism of claim 1, wherein the resiliently flexible member includes a metal and the rest of the second component is a plastic.

15. The attachment mechanism of claim 1, wherein the second component is formed entirely of a single piece of material.

16. An orthopaedic system, comprising:
   a first component having a boss extending from a surface of the first component to a free end, the boss having a non-threaded side wall extending between the free end of the boss and the surface of the first component;
   a second component having a plurality of non-threaded walls defining an aperture in the second component to receive the boss therein wherein at least part of one of the plurality of walls is a resiliently flexible member engineered to apply sufficient force to a part of the side wall of the boss when inserted in the aperture to provide an interference fit between the boss and the plurality of walls of the aperture to releasably retain the boss within the aperture; and
   a third component having a plurality of non-threaded walls defining an aperture in the second component to receive the boss therein, wherein at least part of one of the plurality of walls is a resiliently flexible member engineered to apply sufficient force to a part of the side wall of the boss when inserted in the aperture to provide an interference fit between the boss and the plurality of walls of the aperture to releasably retain the boss within the aperture;
   wherein:
   the second component has a feature and the third component has a corresponding feature;
   the corresponding feature of the third component is different from the feature of the second component;
   the second and third component can be individually selectively and temporarily assembled with the first component by inserting the boss into the aperture of either the second component or the third component and pressing the components together; and
   the assembled components can be disassembled by pulling to detach the components.

17. The orthopaedic system of claim 16, wherein the third component and second component each comprises a shim and wherein the feature is the thickness of each shim.

18. The orthopaedic system of claim 17, wherein the first component is a tibial trial component.

19. A method of manufacturing an orthopaedic apparatus having a first component and a second component which are releasably attachable to each other, comprising:
   forming the first component with a boss extending from a surface of the first component, the boss having a free end and a non-threaded side wall extending from the free end to the surface; and
   forming the second component with a retaining formation comprising a plurality of non-threaded walls defining an aperture to receive the boss therein, and wherein at least part of one of the plurality of walls is a resiliently flexible member engineered to apply sufficient force to a part of the side wall of the boss when inserted in the aperture to provide an interference fit between the boss and the plurality of walls of the aperture to releasably retain the boss within the aperture.

wherein the first and second components can be selectively and temporarily assembled by inserting the boss into the aperture and pressing the components together; and the assembled components can be disassembled by pulling to detach the components.

* * * * *